(12) United States Patent
Matteoni et al.

(10) Patent No.: US 8,254,696 B2
(45) Date of Patent: Aug. 28, 2012

(54) SYSTEMS AND METHODS FOR DETECTION OF AN AIRBORNE CONTAMINANT

(75) Inventors: Joseph Matteoni, St. Charles, MO (US); Jeffery P. Bertram, St. Louis, MO (US); Wayne K. Moore, Gaithersburg, MD (US); Daniel B. Nickell, Vienna, VA (US)

(73) Assignee: DRS Sustainment Systems, Inc., St. Louis, MO (US)

( * ) Notice: Subject to any disclaimer, the term of this patent is extended or adjusted under 35 U.S.C. 154(b) by 997 days.

(21) Appl. No.: 12/044,927

(22) Filed: Mar. 7, 2008

(65) Prior Publication Data

US 2008/0304752 A1     Dec. 11, 2008

Related U.S. Application Data

(60) Provisional application No. 60/893,579, filed on Mar. 7, 2007, provisional application No. 60/893,583, filed on Mar. 7, 2007, provisional application No. 60/893,584, filed on Mar. 7, 2007.

(51) Int. Cl.
*G06K 9/62* (2006.01)

(52) U.S. Cl. ........ 382/209; 382/133; 382/173; 382/128; 382/132; 382/180; 382/217; 382/218; 382/226; 382/227

(58) Field of Classification Search ................ 382/209, 382/133, 173, 128, 132, 134, 180, 217, 218, 382/226, 227
See application file for complete search history.

(56) References Cited

U.S. PATENT DOCUMENTS

| 4,724,394 A * | 2/1988 | Langer et al. ............... 324/464 |
| 7,346,205 B2 * | 3/2008 | Walker, Jr. .................. 382/133 |

FOREIGN PATENT DOCUMENTS

WO     WO2004086941      10/2004

* cited by examiner

*Primary Examiner* — Mike Rahmjoo
(74) *Attorney, Agent, or Firm* — Kilpatrick Townsend & Stockton LLP

(57) ABSTRACT

A method is provided for detection of an airborne contaminant in a atmospheric environment. The method comprises capturing an air sample from the atmospheric environment; separating candidate particles of interest from particles of non interest in the air sample; generating an image of the candidate particles; identifying a contaminant from among the candidate particles by comparing the image of candidate particles with a plurality of stored reference images, each of which reflects a respective identified contaminant; and notifying a remote third party in response to detecting a contaminant from among the candidate particles.

6 Claims, 12 Drawing Sheets

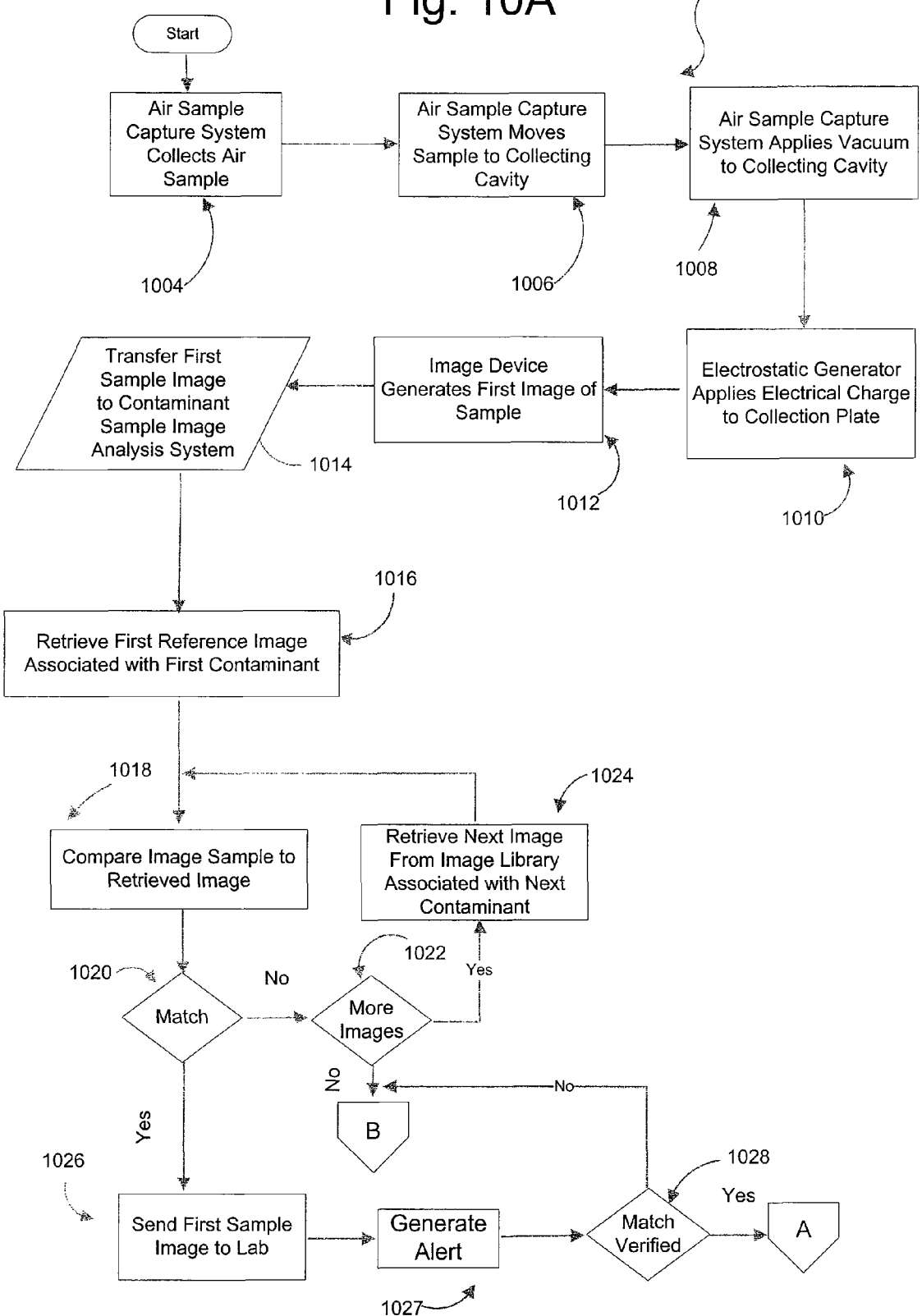

SYSTEMS AND METHODS FOR DETECTION OF AN AIRBORNE CONTAMINANT

CROSS REFERENCE TO RELATED APPLICATIONS

This application claims the benefit of the filing date of U.S. Provisional Applications No. 60/893,579, titled "Systems and Method for the Concentration and Detection of Air Samples," filed on Mar. 7, 2007; U.S. Provisional Application No. 60/893,583, filed Mar. 7, 2007 titled "Systems and Methods for the concentration and Detection of Air Sample Residues"; and U.S. Provisional Applications No. 60/893,584, filed Mar. 7, 2007, titled "Method and Apparatus for Image Detection of Airborne Contaminants", all of which are incorporated herein by reference.

FIELD OF INVENTION

The present invention relates generally to airborne contaminant detection system, and more particularly to systems and methods for capturing an air sample, separating out candidate contaminants from the sample, detecting a contaminant from among the candidate contaminants and alerting a local authority if a contaminant is detected.

The detection of airborne contaminants has received increased attention recently and has resulted in the realization that current airborne contamination detections are inadequate to address the increased risk posed by current world events. The threat of the use of weapons of mass destruction (WMD) has escalated from a controlled circumstance (e.g. weapons of war) to anonymous threats from terrorist groups. Household materials mixed in specific manner may release toxic industrial gases and irritants which may be used to affect large groups of people. Various delivery mechanisms have been identified which are able to dispense airborne contaminants quickly and over large geographic areas. The inclusion of biological material as an airborne contaminant may increase the toxicity of the attack and presents a particularly troublesome issue due to the wide variety and accessibility of biological materials in laboratories, hospitals and university settings. Current airborne contamination detection systems do not provide timely detection to ensure that adequate warning and corrective measures are implemented.

The capture and near real time identification of airborne contaminants, including chemical and biological (C/B) agents, is necessary to properly respond to an attack using weapons of mass destruction. However, the real-time capture and identification of airborne contaminants poses significant challenges including sample capture and preparation without exposure, quick and accurate identification of the agent, immediate warning and implementation of corrective and remediation efforts, and subsequent sterilization of the apparatus used for monitoring and analysis.

Typically, the real-time capture and identification of airborne contaminants is not comprehensive and is limited to very few contaminants using rudimentary spot checks performed in-situ. More comprehensive analysis requires access to a laboratory to accurately analyze and identify the airborne contaminant. For example, an air sample of the local atmosphere may be drawn and isolated in a sampling collecting cavity. The cavity is then transported to a remote laboratory where various testing such as illumination, imaging or irradiating may be accomplished based on the contamination desired to be detected. Many times the concentration of the airborne contaminant is not sufficient to be detected and thus additional processing is required to culture the contaminant before it may be detected is required.

Because the samples being analyzed at the remote laboratory may not all be from the same source, or even the same local atmospheric environment, strict custody control mechanisms must be in place to correctly identify the source of the isolated sample being analyzed. The laboratory may have several stations, each one conducting a separate test, further complicating the custody control of the isolated sample.

Such comprehensive remote laboratory testing is inadequate to deal with the current threat of airborne contamination due to the inability of the current systems to quickly analyze and detect airborne contamination in-situ. For example, remote laboratory analysis is not realistic for monitoring the local atmospheric environment of shipping containers, ventilation ducts, airplane cabins or other confined spaces.

Current in-situ detectors do not perform the comprehensive testing required to identify the myriad of ever changing airborne contaminant threats. Such systems are not adaptable to detect the current expected threat and provide only rudimentary detection similar to that provided by a common smoke detector.

Another problem which plaques such prior art sampling and detection systems is that many samples are required to be drawn due to the number of different tests which must be performed on the samples, as well as the need to ensure the sample adequately represents the atmospheric environment being tested. The requirement for drawing many samples ultimately results in the generation of contaminated sampling equipment which must then be adequately controlled and subsequently sterilized.

Additionally, existing screening systems are generally limited to examination of large boxes and packages, and only screen for items that may be detected by x-ray or similar non-invasive scanners. These systems, while often effective for detecting bombs, are generally unable to detect dangerous powders, liquids, or similar materials. With regard specifically to biologically active agents, generally the defense has not been based in detection, but destruction, by exposing the mail to powerful radiation or other decontaminants in the hopes of neutralizing any biologicals present. Such decontamination, however, generally does not protect against chemical agents, and further can damage the mail, including its contents. Moreover, such decontamination is often performed after mail is sorted, and therefore after many persons may have been exposed.

In order to better protect against dangerous agents in the mails, systems and methods have been developed for the detection of residues sampled from envelopes and other flats of mail. Such a system is described in U.S. Pat. No. 6,941,794, and patents and applications claiming priority thereto, including U.S. Pat. Nos. 7,100,422, 7,073,371, and 7,114,369; and U.S. patent application Ser. Nos. 11/282,268, filed on Nov. 18, 2005, 11/282,740, filed on Nov. 18, 2005, and 11/456,717, filed on Jul. 11, 2006, the disclosure of each such patent and application being incorporated herein by this reference. In at least one of these patents or applications is described a system for detection of residues termed a residue collection module (RCM), also known as a residue collection system. The RCM is particularly directed to obtaining samples of a substance or residue of a substance or a carrier for a substance from internal to an envelope or other mail flat.

In one known embodiment, an RCM comprises an aerosol chamber including an internal area, an intake plenum, the intake plenum being capable of collecting air from the internal area, and at least one array of pinch rollers. The pinch rollers are capable of compressing a mail piece located within the internal area, wherein compression of a mail piece by the pinch rollers can force internal air from within the mail piece out into the internal area of the aerosol chamber, and thereby eject a residue of a substance present in or on the mail piece out into the internal area of the aerosol chamber, wherein the intake plenum can take in at least a portion of the residue from the internal area and can supply the residue to a detection system capable of detecting the residue.

One of the leading problems with aerosolized samples produced by these and other methods for collecting aerosolized samples from mail flats is the large number of particles contained in such samples that are not of interest because they are not the particle of interest nor the residue of interest. For example, pollen, dust, ash, atmospheric microorganisms and other particles are not generally the particle of interest, but are generally contained in the air being sampled. The large number of particles not of interest makes detection of the particles of interest more challenging. For the sake of accurate detection of residues of interest at low concentration, it is desirable to separate particles of interest from the "clutter" of other particles not of interest. Further, such purposeful separation can serve to avoid maintenance problems and increase detector working life by limiting the total number of particles moving through the collection and detection systems.

Accurate and timely warning is paramount to response and reduction in impact of airborne contaminant attack. Accordingly, there is a need for an airborne contaminant detection system that overcomes the problems noted above and previously experienced for capturing an air sample and identifying a contaminant therein. In accordance with the present invention, an airborne contaminant detection system is provided that allows real time diagnosis of both chemical and biological agents.

SUMMARY OF INVENTION

In accordance with systems consistent with the present invention, a system for detection of an airborne contaminant in a detection system is provided. The system comprises a air sample capture system configured to receive an air sample from the atmospheric environment; a contaminant sample separation system effective to receive the air sample from the air sample capture system and to separate particles of interest from particles of non interest in the air sample to form a candidate sample; a contaminant sample imaging device effective to receive a candidate sample from the contaminant sample separation system and generate an image of the candidate sample; and a contaminant sample imaging analyzing system effective to receive a contaminant image sample from the contaminant sample imaging system and detect the presence of a contaminant in the candidate sample by comparing the candidate sample images with a plurality of stored reference images, each of which reflects a respective identified contaminant.

In accordance with methods consistent with the present invention, a method is provided for detection of an airborne contaminant in a atmospheric environment. The method comprises capturing an air sample from the atmospheric environment; separating candidate particles of interest from particles of non interest in the air sample to form a candidate sample; generating an image of the candidate sample; identifying a contaminant from among the candidate particles by comparing the candidate sample image with a plurality of stored reference images, each of which reflects a respective identified contaminant; and notifying a remote third party in response to detecting a contaminant from among the candidate particles.

Other systems, methods, features, and advantages of the present invention will be or will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF DRAWINGS

The accompanying drawings, which are incorporated in and constitute a part of the specification, illustrate implementations of the present invention and, together with the description, serve to explain the advantages and principals of the invention. In the drawings:

FIGS. 10A and 10B depict a flow diagram illustrating an exemplary process performed by the airborne contaminant detection system for detecting contaminants in a local atmospheric environment in accordance with the present invention.

DETAILED DESCRIPTION OF THE INVENTION

Figure 1:
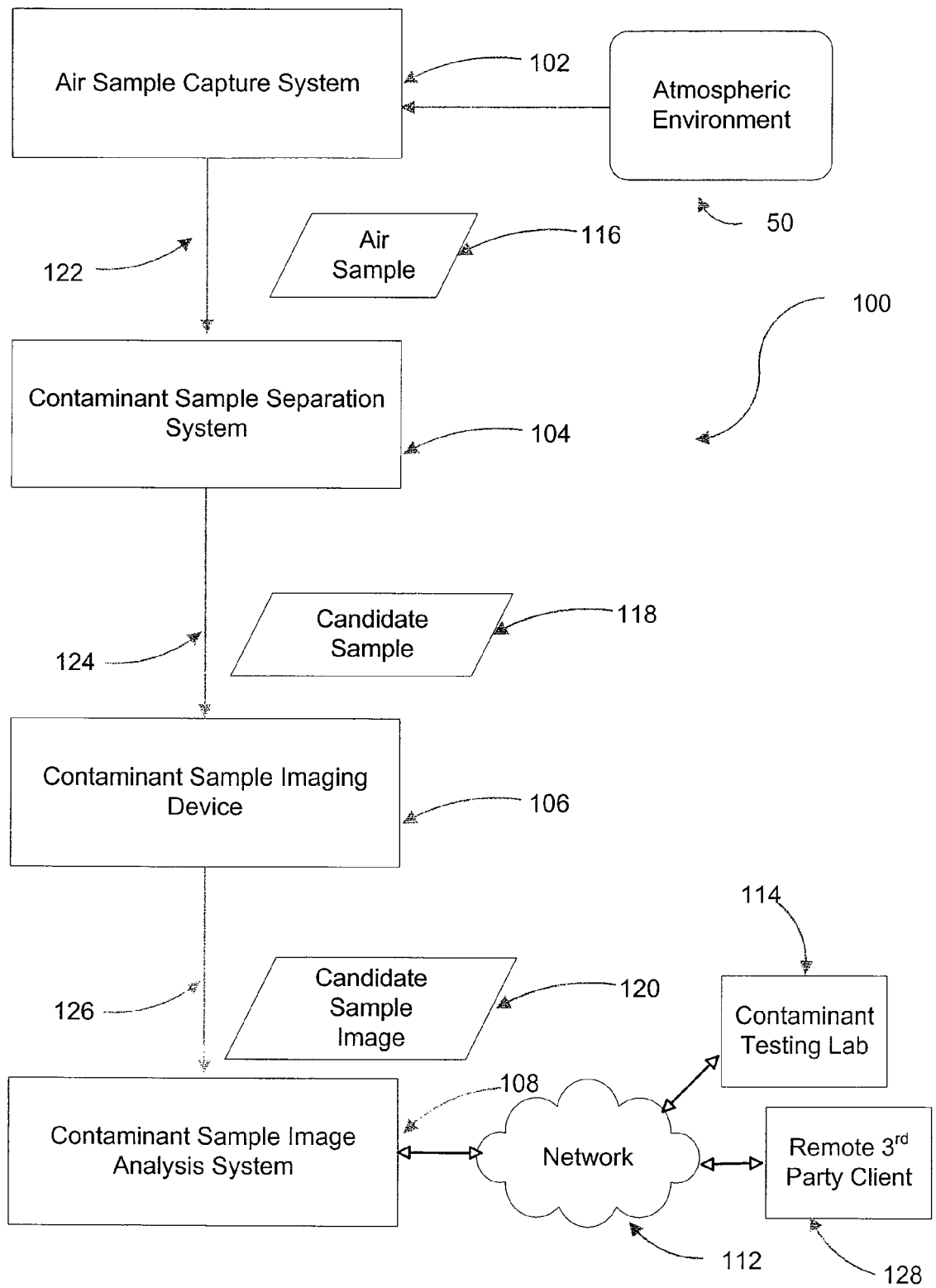
FIG. 1 is a simplified pictorial representation of an airborne contaminant detection system consistent with the present invention.

Referring now to the drawings, FIG. 1 depicts an airborne contaminant detection system 100 consistent with the present invention. The airborne contaminant detection system 100 includes an air sample capture system 102, a contaminant sample separation system 104, a contaminant sample image device 106, and a contaminant sample imaging analysis system 108, which may be operatively connected to a contaminant testing lab 114 and a remote third party 128 via a network 112. The network 112 may be any known private or public communication network such as a Local Area Network ("LAN"), Wide Area Network ("WAN"), Peer-to-Peer Network, or the Internet, using standard communication protocols. The network may include hardwired as well as wireless branches.

As demonstrated in FIG. 1 and discussed in further detail herein, the air sample capture system 102 is operatively configured to capture an air sample 116 from an atmospheric environment 50 surrounding or in proximity to the air sample capture system 102. In one embodiment, the air sample capture system 102, may be a residue collection module (RCM) as described in U.S. Pat. No. 6,941,794 titled "Systems and Methods for Residue Collection," an intake plenum is adapted to collect air from the atmospheric environment 50 local to the RCM. The intake plenum is adapted to supply the air sample 116 to a contaminant sample separation system 104 via piping 122 such as PVC piping or other suitable piping. In another embodiment, the air sample capture system 102, may be a cyclonic separator as described in U.S. Patent Publication 2005/0223685 titled "Cyclonic Separator with Secondary Vortex Break," is adapted to collect air from the atmospheric environment 50 local to the cyclonic separator. The cyclonic separator is adapted to supply the air sample 116 to a contaminant sample separation system 104 via a piping 122 such as PVC or other suitable piping. In yet another embodiment, the air sample capture system 102 may comprise a person collecting air samples using a container and manually supplying the air sample 116 to the contaminant sample separation system 104.

In accordance with the present invention, the air sample 116 is transmitted via piping 122 or manually delivered to the contaminant sample separation system 104 which separates candidate contaminants from non-contaminants to form a candidate sample 118 as discussed in detail below. After the contaminants are separated, the contaminant sample separation system 104 transfers the candidate sample 118 to a contaminant sample imaging device 106 via piping 124 which may be PVC or other suitable piping. The contaminant sample imaging device 106 is operatively configured to receive the candidate sample 118 from the contaminant sample separation system 104 via the piping 124 and to generate an image (e.g. candidate sample image 120) of the candidate sample 118 or of the candidate contaminants therein.

In further accordance with the present invention, the contaminant sample imaging device 106 is communicatively coupled to a contaminant sample image analysis system 108 via a communication link or network 126. The communication link or network 126 may be any known private or public communication link or network such as Firewire, USB, LAN, WAN, Peer-to-Peer, or the Internet, using standard communication protocols. The communication link or network 126 may include hardwired as well as wireless branches.

In further accordance with the present invention, the contaminant sample image analysis system 108, as described in detail below, is configured to receive the candidate sample image 120 from the contaminant sample image device 106 via the network 126. The contaminant sample imaging analysis system 108 is operatively configured to compare the candidate sample image 120 with a plurality of reference images, each of which reflects a known or identified contaminant such as anthrax or other known chemical or biological agents. The contaminant sample image analysis system 108 is adapted to detect a contaminant if the candidate sample image 120, matches one of the plurality of reference images. The contaminant sample image analysis system 108 is also configured to generate an alert over the network 112 to a remote authorities or third party client 128, such as the local police or fire department so that the authorities or third party may evacuate the area or perform some other action to control the spread of the contaminant, upon the detection of a contaminant.

Air samples 116 that are collected in the air sample capture system 102 may contain only dilute concentrations of the particles of interest, especially if the air sample 116 is mixed with ambient air (e.g. within an aerosol chamber that may be employed in the RCM embodiment of the air sample capture system). Thus, the candidate contaminant or particulates of interest in such an air sample 116 may require concentration prior to their detection. Such concentration may be particularly useful for detecting very low levels of the particulates of interest in the air sample 116. For instance where the particles of interest include chemical or biological agents that may be harmful at very low levels, low level detection is highly desired, and therefore concentration of the air samples 116 may be important.

Figure 2:
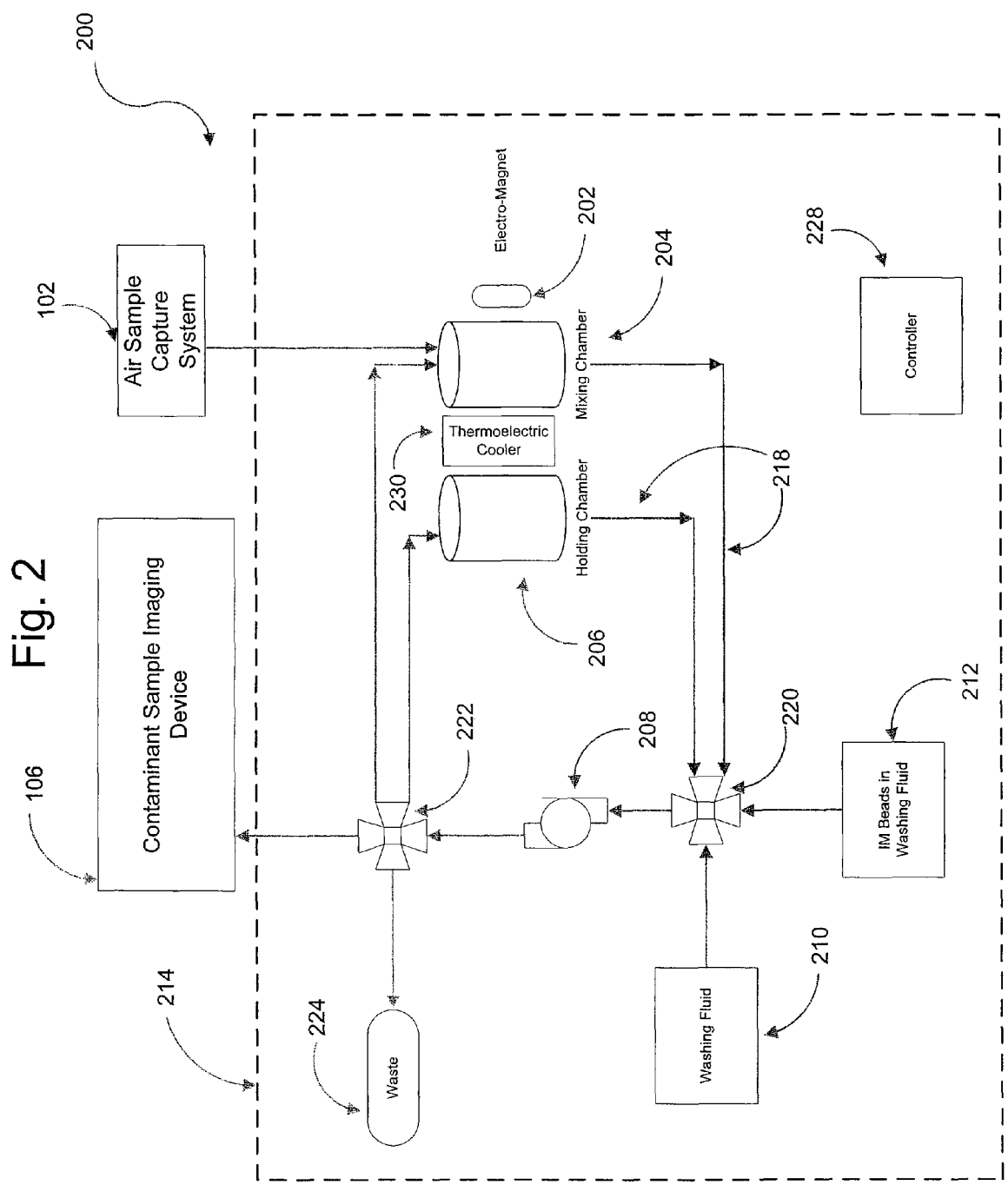
FIG. 2 is a simplified pictorial view of one embodiment of a contaminant sample separation system of the system in FIG. 1, where the contaminant sample separation system separates candidate particles from particles of non interest in a captured air sample in accordance with the present invention.

FIG. 2 is a simplified pictorial view of one embodiment of a contaminant sample separation system of the system in FIG. 1, where the contaminant sample separation system 200 separates candidate particles from particles of non interest in a captured air sample in accordance with the present invention. The contaminant sample separation system 200 shown in FIG. 2 employs a wet concentration method to concentrate the particles in the air sample 116 as further described below. The contaminant sample separation system 200 comprises a mixing chamber 204 having an input for receiving an air sample 116 from the air sample capture system (e.g. via piping 124 or manual input) and an output in fluid communication with a first port of a first 5-way valve 222, a pump 208 in fluid communication with a second port of the first 5-way valve 220 and a first port of a second 5-way valve 222, a washing fluid container 210 in fluid communication with a third port of the first 5-way valve 220, an immunomagnetic bead supply 212 in fluid communication with a fourth port of the first 5-way valve 220, a waste container 224 fluid communication with a second port of the second 5-way valve 222, and a holding chamber having an input in fluid communication with a third port of the second 5-way valve 222 and an output in fluid communication with the fourth port or a fifth port of the first 5-way valve 220. As shown in FIG. 2, the input of the mixing chamber 204 may also be connected to a fifth port of the second 5-way valve 220 in order to receive a preliminary or dirty sample contained in the holding chamber 206 as further described below. The contaminant sample separation system 200 may also include an electromagnet 202 disposed in relation to the mixing chamber 204 such that the electromagnet 202 is effective to draw magnetic particles away from the contaminant sample to be generated. The contaminant sample separation system 200 may also include an thermoelectric cooler 230 disposed in relation to the mixing chamber 204 such that the thermoelectric cooler 230 is effective to reduce the temperature of the sample in mixing chamber 204. The contaminant sample separation system 200 further includes a controller 228 which may implemented in hardware (such as an ASIC device) or in hardware and software (such as a microprocessor operatively configured to run a program in memory) to control the valves 220 and 222, the pump 208, and other components (such as the optional electromagnet 202 and the optional thermoelectric cooler 230) with controlled inputs or outputs to operate the contaminant sample separation system 200 as described herein.

The air sample 116 captured by the air sample capture system 102 or manually is transferred into the mixing chamber 204, for combination with a wet concentrate such a fluid stored in the washing fluid container 210. The initial sample mixture formed in the mixed chamber 204 after the air sample 116 is introduced into the chamber 204 is referenced as a "dirty sample" as the initial sample mixture may contain particles of interest (e.g., candidate contaminants) as well as many particles not of interest (e.g., non-contaminants). In another embodiment, the dirty sample that is initially formed or contained in the mixing chamber 204 may have a volume in the range of about 1 mL to about 10 mL.

In one implementation, to avoid interference in later particle separation steps, magnetic particles may first be removed from the dirty sample, prior to adding immunomagnetic beads 308 from supply 212 for separating out the particles of interest to form a candidate sample 118. When energized by the controller 228, the electromagnet 202 generates a magnetic field in the mixing chamber 204 which is effective to immobilize any magnetic particles in the dirty sample. The controller 228 then causes the dirty sample to be pumped out of the mixing chamber 204 via the pump 208 to the holding chamber 206 through the 5-way valve 220 and the second 5-way valve 222 and piping 218, leaving behind the "dirty" magnetic particles in the mixing chamber 204. Next, the controller 228 de-energizes the electromagnet 202 to remove the magnetic field in the mixing chamber 204 and then causes the "dirty" magnetic particles remaining in the mixing chamber 204 to be flushed to the waste container 224 through the 5-way valve 220, pump 208, and 5-way valve 222 via piping 218 after the magnetic field is removed. The removal of magnetic particles prior to the addition of immunomagnetic beads 308 from the supply 212 may be performed more than once, preferably twice. In an alternate embodiment, this process of removing magnetic particles from the dirty sample prior to adding immunomagnetic beads is omitted.

To perform the separation of particles of interest from particles not of interest, immunomagnetic beads from the immunomagnetic beads supply 212 are mixed with the dirty sample. Immunomagnetic particles or beads for this purpose are commercially available from Dynabeads (Dynal Inc., Oslo, Norway) and EMD Biosciences (Merck KGaA, Darmstadt, Germany) under the Calbiochem brand. In one embodiment the immunomagnetic bead supply 212 comprises a buffered suspension of immunomagnetic beads 212 having a diameter of about 4.5 microns. In one implementation in which the "dirty" magnetic particle content of the dirty sample first has been reduced, the dirty sample contained in the holding chamber 206 is pumped back to the mixing chamber 204 via the pump 208, the 5-way valve 220, the second 5-way valve 222 and piping 218 after the "dirty" magnetic particles have been washed out of the mixing chamber 204. As further discussed herein, immunomagnetic beads (308 in FIG. 3) contained in supply 212 each have an antibody for a particular particle of interest 310 bound to their surface of the respective bead 308. After the "dirty" magnetic particles have been washed out of the mixing chamber and the dirty sample contained in the holding chamber is pumped into the mixing chamber 204 and mixed with the dirty sample the immunomagnetic beads are added to the mixing chamber from the supply 212 via the 5-way valve 220, the pump 208 and the second 5-way valve 222.

The immunomagnetic beads 308 are mixed in the mixing chamber 204 with the dirty sample in a ratio of 40,000,000 beads per milliliter of dirty sample. In one implementation, the beads 308 and the dirty sample are mixed at a predetermined temperature of about 4° C. or less for about thirty (30) minutes (as controlled by the thermoelectric cooler 230 via the controller 228) in the mixing chamber 204, during which time the particle of interest 306 (in FIG. 3) binds to the beads 308. The electro-magnet 202 is then energized generating a magnetic field in the mixing chamber, thereby immobilizing the immunomagnetic beads 308. The remaining dirty sample (which does not include the immobilized immunomagnetic beads 308) is transferred to waste 224 from the mixing chamber 204 through the 5-way valve 220, the pump 208, and the second 5-way valve 222 via piping 218. The immunomagnetic beads 308 immobilized in the mixing chamber 204 are then washed with fresh wash fluid from the washing fluid container 210. The wash fluid in the mixing chamber 204 is then transferred to the waste container 224 through the 5-way valve 220, the pump 208, and the second 5-way valve 222 via piping 218. Next, the immunomagnetic beads 308 may be released from magnetic immobilization caused by the electro magnet 202 in order to be re-mixed in the mixing chamber 204 with additional wash fluid 210 from the washing fluid container 210 prior to the beads 308 again being magnetically immobilized by the electromagnet 202 in the mixing chamber 204 to allow the wash fluid to be removed through 5-way valve 220, the pump 208, and the second 5-way valve 222 via piping 218.

The beads 308 are washed two or more times, with the electromagnet 202 immobilizing the beads 308 between washes in order to flush out the used wash fluid 210. In a preferred embodiment, four such washes are performed. After the last wash, the beads 308 (to which the particles 306 are bound) in the mixing chamber 204 are suspended in wash fluid from the wash fluid container 210 and transferred as a candidate sample 118 to the contaminant sample imaging system 216 through the 5-way valve 220, the pump 208, and the second 5-way valve 222 via piping 218 where detection of the particle is carried out.

In another embodiment, the immunomagnetic bead separation system 214 processes the output from more than one contaminant sample imaging system 216. Four samples are delivered to the immunomagnetic bead separation system 214. In another embodiment, the air samples from more than one air sample capture system 102 are either simultaneously or sequentially delivered to the mixing chamber 204 via piping 218 or manually. In a preferred embodiment, once each of the samples from the more than one air sample capture system 102 has been delivered to the mixing chamber 204 via piping 218, the separation process—through which the particle of interest 306 is separated from other particulates using immunomagnetic beads 308—may be performed as discussed herein.

Figure 3:
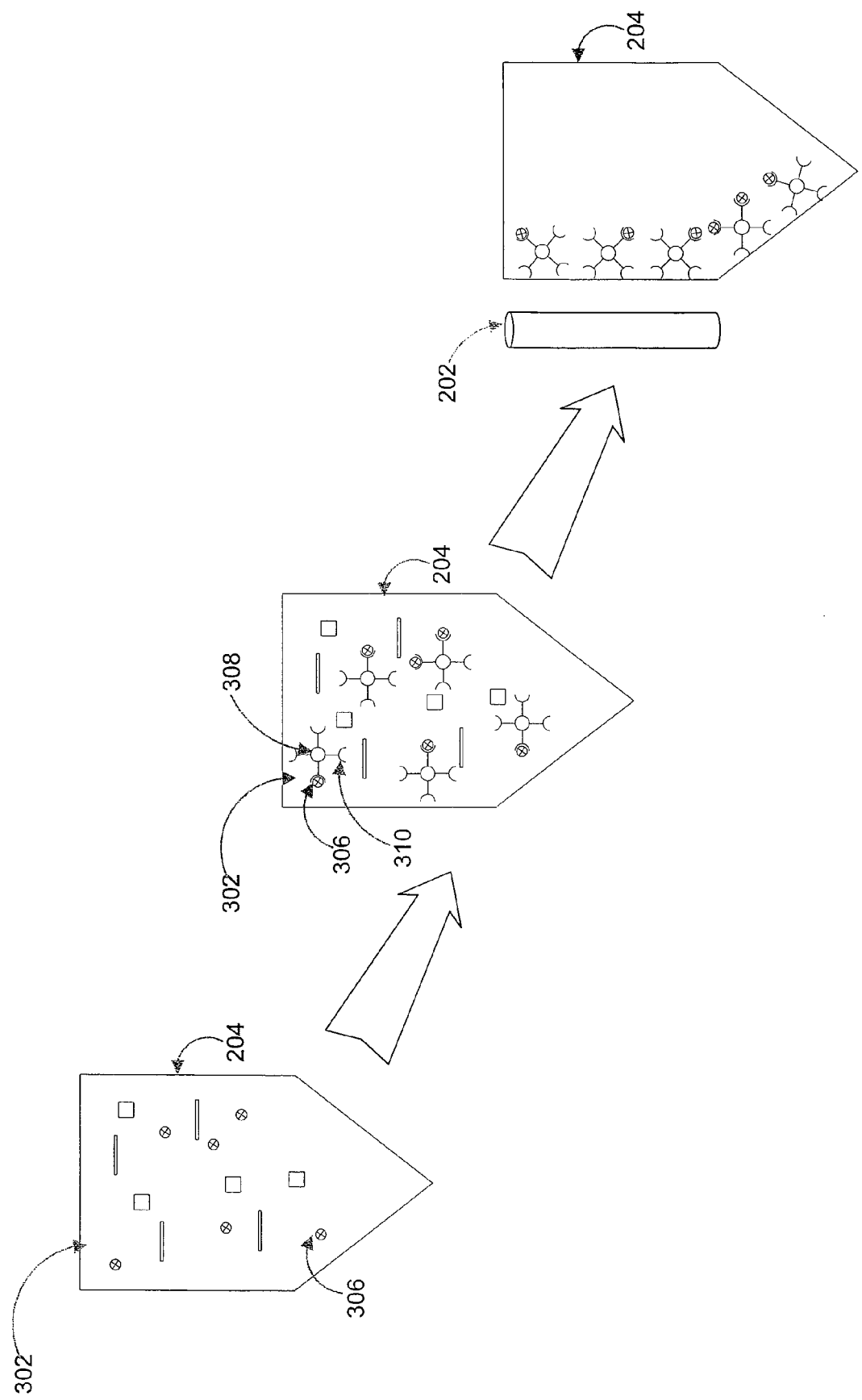
FIG. 3 is a functional block diagram of an immunomagnetic bead separation process performed by the contaminant sample separation system in FIG. 2 in accordance with the present invention.

FIG. 3 is a functional block diagram of a immunomagnetic bead separation process performed by the contaminant sample separation system 200 as discussed herein in accordance with the present invention. As previously discussed, the "dirty" sample 302 initially formed in the mixing chamber 204 from an air sample 116 may include particles of interest (candidate contaminants) along with other particles (non contaminants) that may potentially interfere with the analysis and detection of the particle of interest. As shown in FIG. 3 as part of the separation process, immunomagnetic beads 308 are added to the dirty sample 302 in the mixing chamber 204. As further shown in FIG. 3, upon mixing of the immunomagnetic beads 308 and the dirty sample 302, the antibodies 310 (bound to the beads 308) further bind the antigens 306, which are the particle of interest. As previously described, when the electromagnet 202 is energized a magnetic field is generated in the mixing chamber 204 (as illustrated in FIG. 3 by a electromagnet 202), causing the immunomagnetic beads 308 having the particle of interest 306 to be immobilized to a side of the mixing chamber 204. While the immunomagnetic beads 308 are immobilized, other particles in the sample 302 are flushed out of the mixing chamber 204 using washing fluid from the washing fluid container 210. The use of immunomagnetic beads allows further concentration of the particle of interest to allow further increases in detection sensitivity above the levels of sensitivity achieved in analysis without the immunomagnetic beads. In an alternate embodiment, the use of immunomagnetic beads allows for alternate methods of detection, including visual detection (e.g., by microscope) of the particle attached to the bead.

Once the particle of interest 306 has been separated from other particles not of interest through binding to the beads 308, the particle 306 may be detected while the particle is bound to the bead 308 or while the particle is decoupled from the bead 308.

In one embodiment, separation of the particle of interest 306 from the dirty sample is followed by visual detection of the presence of the particle of interest 306 using a contaminant sample imaging device 106 comprising a microscope or other magnification lens or by the human eye. For example, visual detection of the particle of interest 306 is possible when the particle of interest 306 is a species of bacterium, such as Bacillus globig10 or Bacillus anthracis, that has been bound to an immunomagnetic bead 308. Other species of bacterium, as well as other biologic and chemical particles are also visually detectable. The bacterium or its endospore or other particle (e.g., biologic or chemical particle) bound to the immunomagnetic bead causes an alteration in visible light, e.g., a diffraction or refraction, that is different from that of the bound bead, such that the bacterium or endospore or other particle may be observed as a distinct spot adjacent to the immunomagnetic bead when viewed, for instance, under a microscope.

Figure 4:
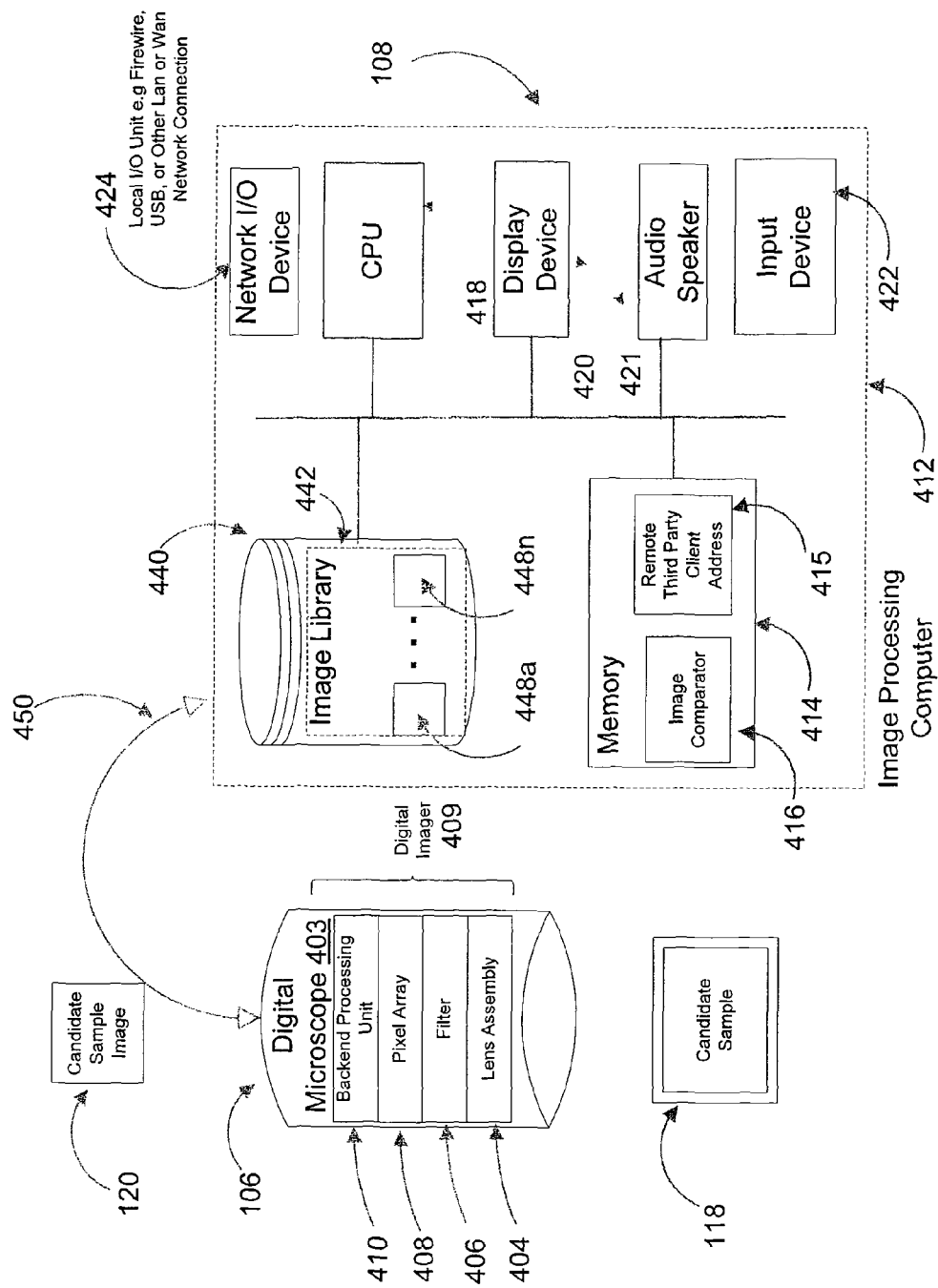
FIG. 4 is a simplified pictorial view of one embodiment of the contaminant sample imaging device and a contaminant sample image analysis system employed in the system FIG. 1.

FIG. 4 is a simplified pictorial view of one embodiment of the contaminant sample image device 106 that may be used to generate a candidate sample image 120 from a candidate sample 118. The contaminant sample imaging device includes a digital microscope 403 and digital imager 409. The digital microscope 403 and digital imager 409 may share a lens assembly 404 for viewing the candidate sample with the human eye. The digital imager 409 further includes a filter 406 for isolating the wavelength spectrum of interest, a pixel array 408 for capturing a image frame of the candidate sample 118 and a back end processing unit 410 for processing the one or more image frames to generate a candidate sample image 120. The digital imager 409 is communicatively coupled to an image processing computer 412 via a network 450. The network 450 can include any known network including Firewire, USB, LAN, WAN, Peer-to-Peer Network, or the Internet, using standard communication protocols. Each candidate sample image 120 generated by digital imager 409 is transferred to the image processing computer 412 via the network 450.

The image processing computer includes a network I/O device 424, a CPU 418, a display device 420, a input device 422 such as a keyboard or mouse, a audio speaker 421, a memory 414 and a secondary storage 440 holds a image library 442 having a plurality of reference images or files 448a-448n each of which reflects an identified or known contaminant. The network I/O device 424 of the image processing computer 412 is operatively configured to receive each candidate sample image 120 from the network 450 and store the image 120 in memory 414 for processing by a image comparator 416 program stored in the memory 414 as further discussed below. The image comparator 416 is operatively configured to access the image library 440 and each image reference file 448a-448n therein. The image comparator program 416 as run by the CPU 418 performs a process to compare the candidate sample image 120 with one or more of the image reference files 448a-448n to detect a contaminant and alert a remote authority or third party 102 of the detected contaminant. The memory 414 may also have a address 415 of the remote authority or third party client 128. The address 415 may be a network address (e.g. IP address or e-mail address) or a telephone number. The image comparator 416 is operatively configured to access the address 415 to notify the remote authority or third party client 128 in the event that the image comparator 416 identifies a contaminant in a candidate sample image 120 as discussed in further detail herein.

Figure 5:
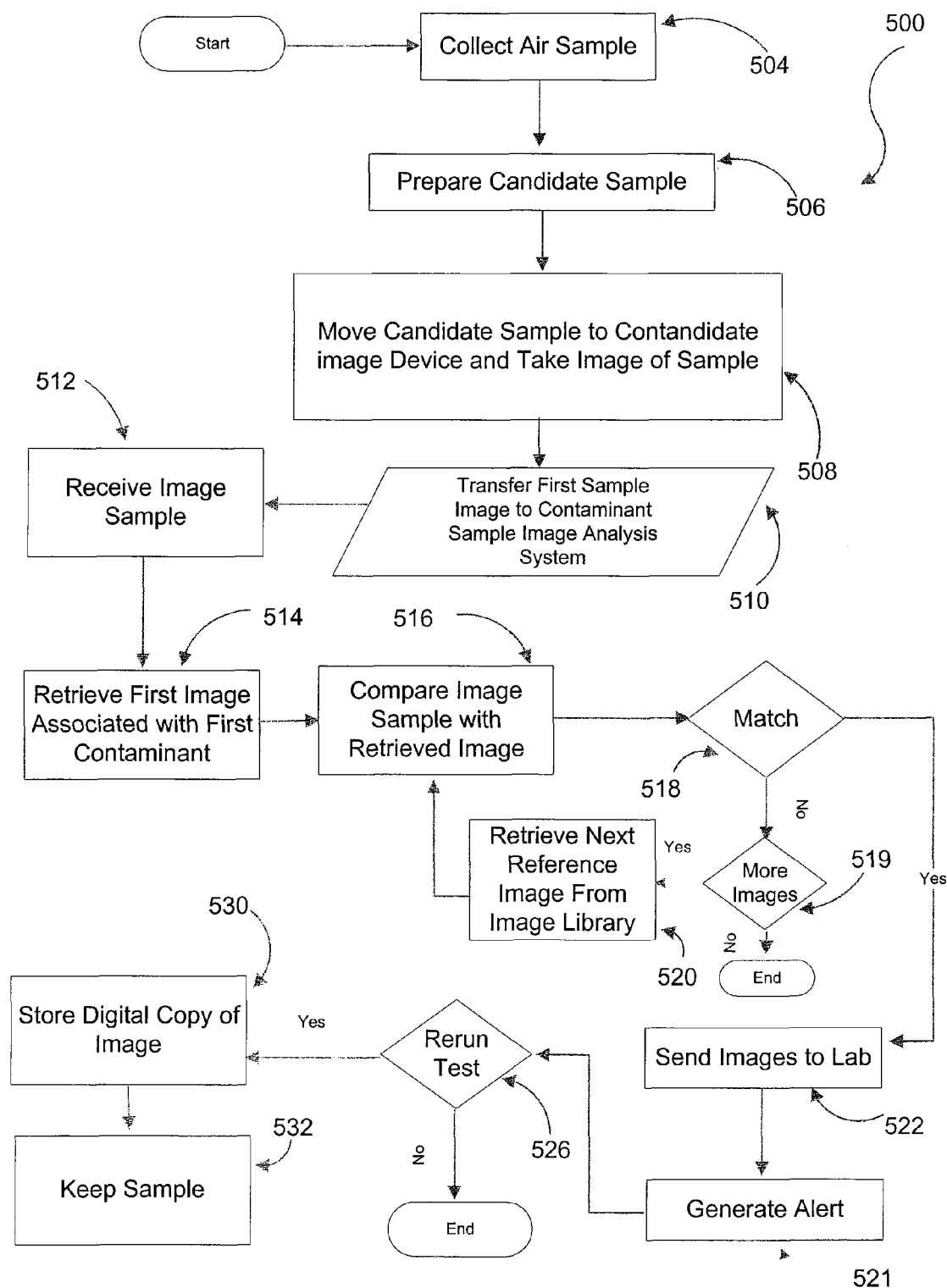
FIG. 5 depicts a flow diagram illustrating another exemplary process performed by the airborne contaminant detection system for detecting a contaminant in a local atmospheric environment in accordance with the present invention.

FIG. 5 is a flow diagram depicting an exemplary process 500 performed by the airborne contaminant detection system 100 embodying the contaminant separation system 200 to capture an air sample, separate contaminant particles within the air sample, and alert a remote authority in the event a contaminant is identified. Initially, an air sample 116 is collected by the air sample capture system 102 and is then provided to the contaminant sample separation system 200 (step 504). Next, a candidate sample separation system 200 generates a candidate sample 118 as discussed above (step 506). After the candidate sample 118 is generated, the candidate sample 118 is transferred by the contaminant sample separation system 200 to the contaminant sample image device 106 manually, through piping 124 or other transfer methods (step 508). Upon receiving the candidate sample 118, the contaminant sample image device 106 then generates a candidate sample image 120 of the candidate sample 118 and transmits the candidate sample image 120 to the contaminant sample image analysis system 108 via network 126 for analysis (step 510).

As shown in FIGS. 4 and 5, the candidate image sample 120 is sent to a imaging processing computer 412 (step 512). Next, the image processing computer 412 of the contaminant sample image analysis system 108 receives the candidate image sample via the network I/O device 424. The imaging processing computer 412 retrieves a first image (e.g. 448a) associated with a first contaminant (step 514). The image processing computer 412 than compares the candidate sample image 120 with the retrieved image (step 516). The image comparator 416 then determines whether the candidate sample image 120 substantially matches the retrieved image (step 518). If a match does not occur, the image comparator 416 determines whether there are more reference images in the image library 442 (step 519). If there are no more reference image files, the image comparator 416 ends processing. If there are more reference images in the image library 442, the image comparator 416 retrieves a next reference image file (e.g. 448n) from the image library 442 for comparison against the candidate sample image 120 (step 520) before continuing processing at step 516.

If a match occurs, the image comparator 416 generates an alert over the network 112 to a remote authorities or third party client 128 using the address 415 stored in memory, such as the local police or fire department so that the authorities or third party may evacuate the area or perform some other action to control the spread of the contaminant. In addition, if a match occurs, the image comparator 416 transmits the candidate sample image 120 to a contaminant testing lab 114 (step 522) which may independently verify the candidate sample image 120 in response to the identified contaminant. Next, the image comparator 416 may rerun the steps 516, 520, 519 and 518 to verify that the candidate sample image 120 matches the retrieved image previously determined to contain a identified contaminant (step 526). If a match is verified, the candidate sample 118 is saved along with a candidate sample image 120 before processing ends (steps 530 and 532).

Figure 6:
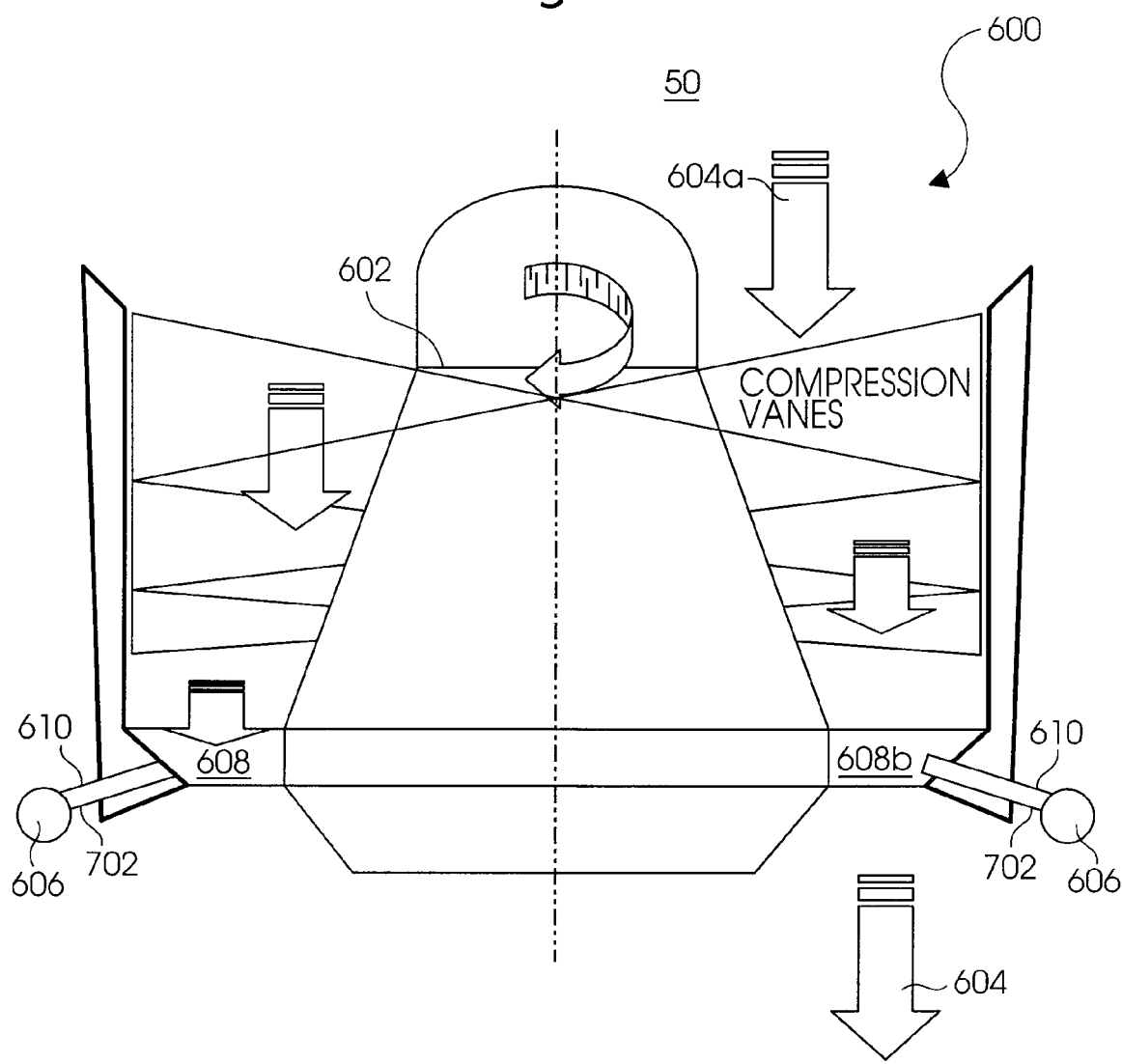
FIG. 6 is a cross sectional pictorial view of an another embodiment of the contaminant separation system in accordance of the present invention.

FIG. 6 is a cross sectional pictorial view of an another embodiment 600 of the contaminant sample separation system 104 employed in the airborne contaminant detection system 100 in accordance of the present invention. In one implementation, the contaminant sample separation system incorporates the air sample capture system 102 or aspiration and air capture function by using a combination of centrifugal airflow and vacuum aspiration. As shown in FIG. 6, the contaminant sample separation system 600 includes a centrifugal turbine or impellor 602 that draws a sample of air 604 from the local atmospheric environment 50 and compresses the sample (e.g., compressed sample 604b). The act of compressing concentrates any contaminants contained in the sample 604b in an outlet plenum 408. The contaminant sample separation system 600 further includes one or more collecting cavities (e.g., collecting cavity 702 in FIG. 7) each of which is adapted to receive the compressed sample 604b (or a portion thereof) from an outlet plenum 608 of the centrifugal turbine or impellor 602.

Figure 7:
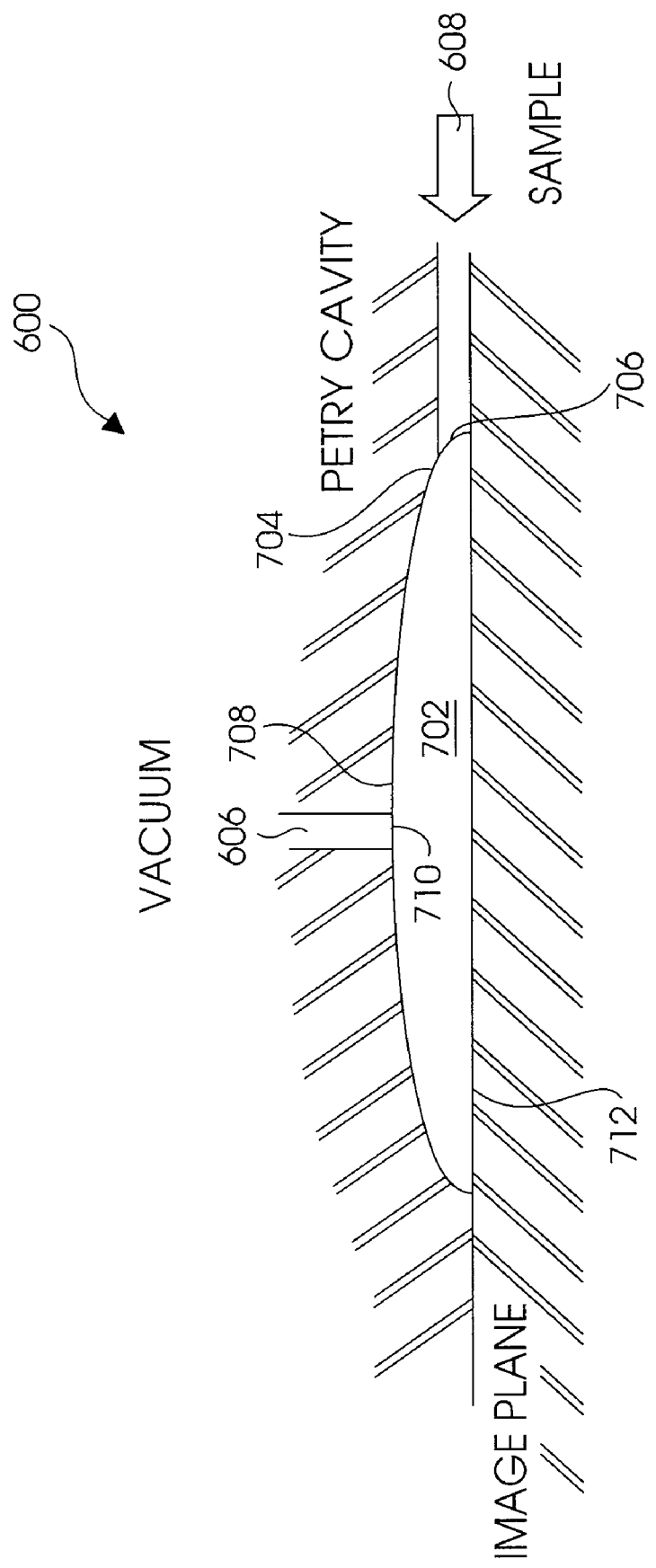
FIG. 7 is a cross sectional pictorial view of a collecting cavity implemented in the contaminant separation system of FIG. 6.

In one implementation, the contaminant sample separation system 600 further includes a vacuum ring 606 that is adapted to apply a vacuum to each collecting cavity 702 to facilitate the aspiration of the sample from the outlet plenum 608 to the collecting cavity 702. FIG. 7 illustrates a cross sectional pictorial view of one collecting cavity 702 disposed between the vacuum ring 606 and the outlet plenum 608. As shown in FIG. 7, the collecting cavity may have a first side 704 defining a first opening 706 in gas or fluid communication with the outlet plenum 608 and a second side or top 708 that defines a second opening 710 operatively connected to the vacuum ring 606 such that the vacuum ring 606 may apply a vacuum to the collecting cavity 702 to facilitate the aspiration of the compressed sample 604b from the outlet plenum 808 to a surface 712 of the collecting cavity 720. The compression of the sample 604b in the collecting cavity 702 may increase the concentration of the airborne contaminants sufficiently to obviate the necessity of culturing an air sample as typically required in prior art remote laboratory analysis.

Figure 8:
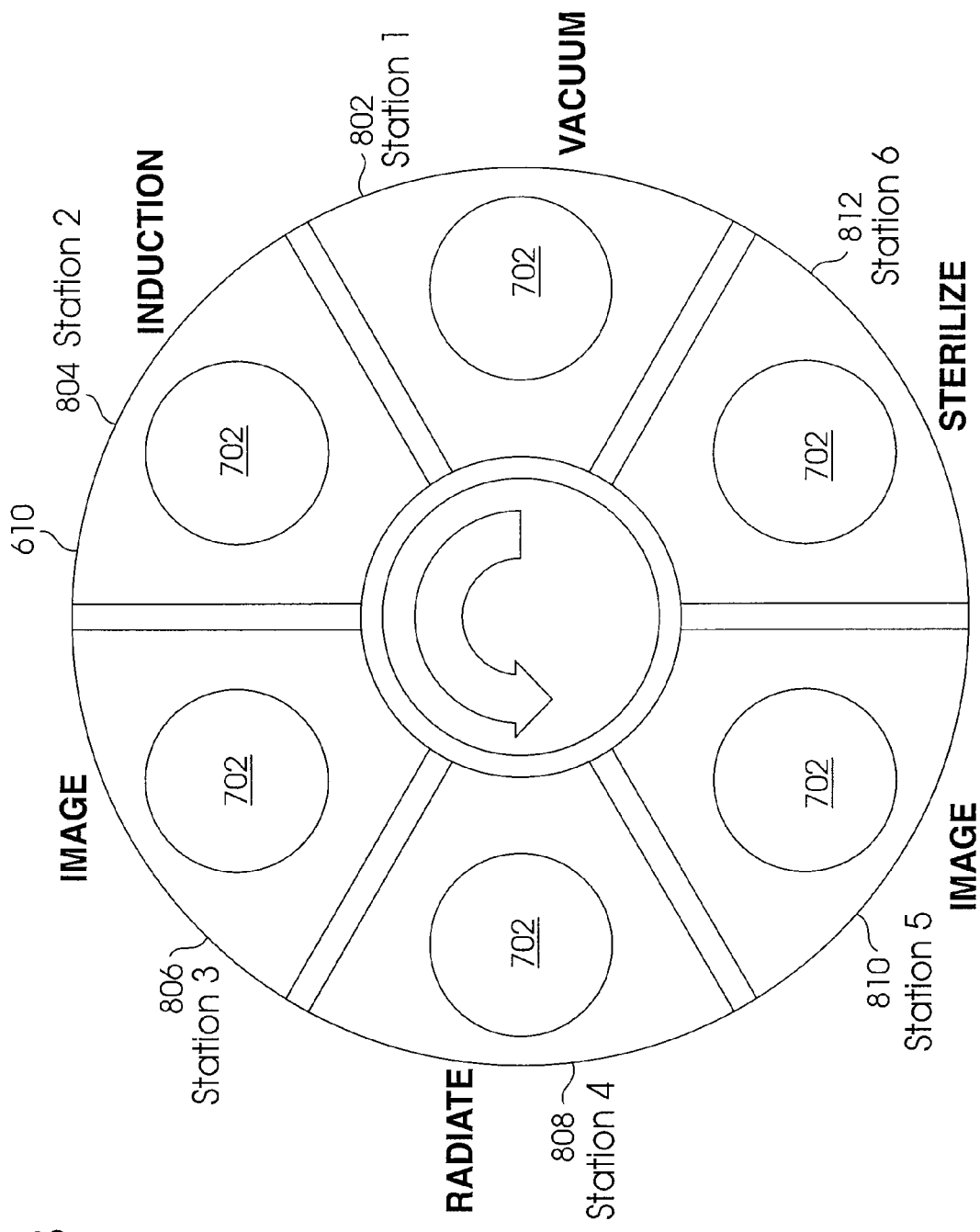
FIG. 8 is a top level simplified pictorial view of an indexing table suitable for use with the contaminant separation system of FIG. 6.
Figure 9:
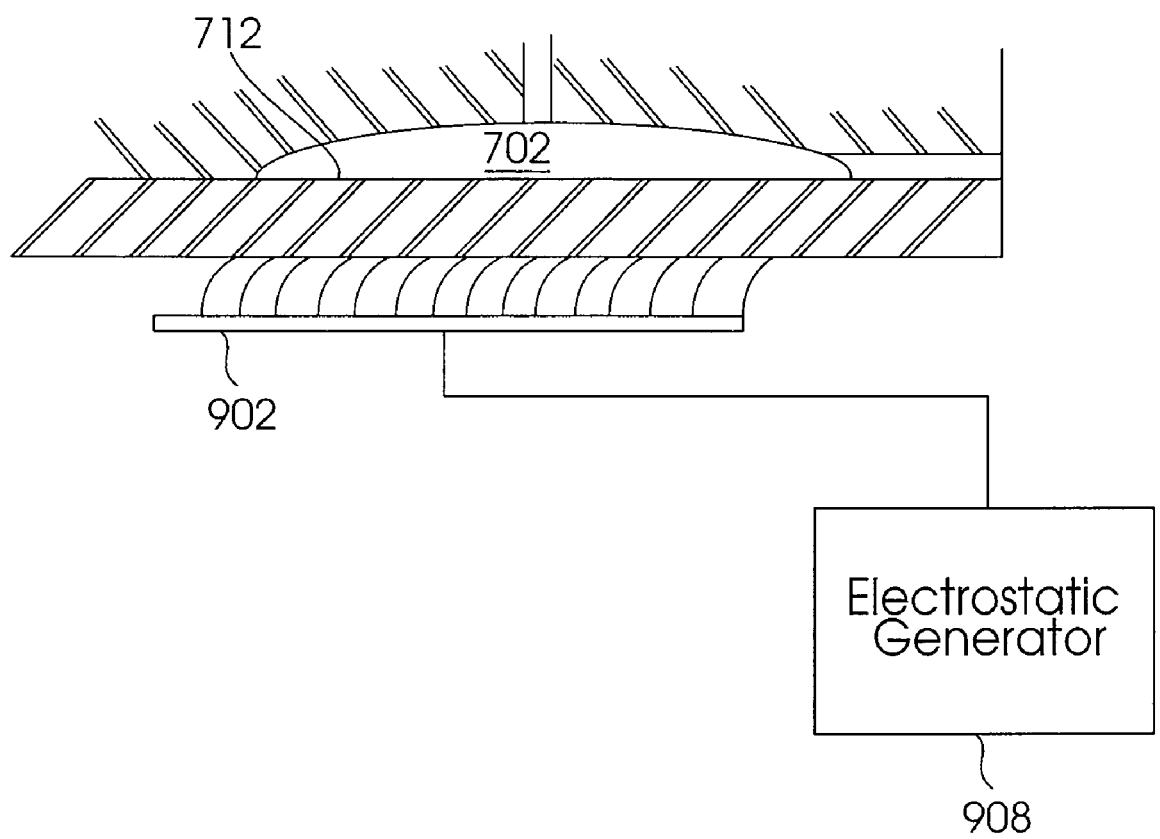
FIG. 9 is a simplified cross sectional pictorial view of the collecting cavity of FIG. 5 and a static charge device adapted to apply a static charge to the collecting cavity.

In one implementation, the contaminant sample separation system 600 further includes an indexing table 610 as shown in detail in FIG. 8. The indexing table 610 includes the collecting cavities 702 arranged circumferentially about the indexing table 610. The indexing table 610 is adapted to rotate about its center to enable sequential samples 604b to be received by respective collecting cavities 702 from the outlet plenum 608. The indexing table 610 may provide the samples 604b to a series of stations for further processing an analysis. For example, FIG. 8 illustrates an indexing table 610 for use with an airborne contaminant detection system 600 having six stations 802, 804, 806, 808, 810 and 812. In operation, the indexing table 410 places a first collecting cavity 702 in gas or fluid communication with the outlet plenum 608 to draw a first compressed sample 604b into the first collecting cavity 702 corresponding to or aligned with a first station 802. As long as the pressure in the outlet plenum 608 is greater than the pressure in the collecting cavity 702 aligned with the first station 802, the compressed sample 604b will be drawn in to the respective collecting cavity 702. A vacuum ring 606 or source, as discussed above with respect to FIG. 7, may be utilized to assist in aspirating the compressed sample into the respective collecting cavity 702 aligned with the first station 802.

When the collection of the first sample at the first station 802 is complete, the indexing table 610 rotates the collecting cavity 702 to the second station 804. As the first sample rotates to the second station 804, another collecting cavity 702 is moved to the first station 802 to receive a second compressed sample from the outlet plenum 608. Although the indexing table 610 of FIG. 8 illustrates how six compressed samples may be processed simultaneously, the present discussion will be limited to the processing of the first compressed sample with the understanding that the other five compressed samples undergo similar processing.

As the compressed sample 604b is moved from the first station 602 to the second station 604, an electric charge is applied to the surface 712 (which may be a flat surface) of the collecting cavity 502 to attract any entrained contaminants in the compressed sample 604b to the surface 712 or focal plane of the collecting cavity 702. The charge applied to the collecting cavity 702 may be produced by any convention electrical induction means such as via electrostatic generator 708 as shown in FIG. 7. For example, in one implementation, the contaminant sample separation system 600 includes an electrostatic comb 902 electrically connected to an electrostatic generator 908. In this implementation, the electrostatic comb 902 is positioned beneath the indexing table 610 between the first 802 and second stations 804 such that the comb 902 applies a static charge (received from the electrostatic generator 908) to the surface 712 of the collecting cavity 702 when the respective collecting cavity 702 is aligned with station 802 and before or during rotation towards the second station 804.

Figure 10B:
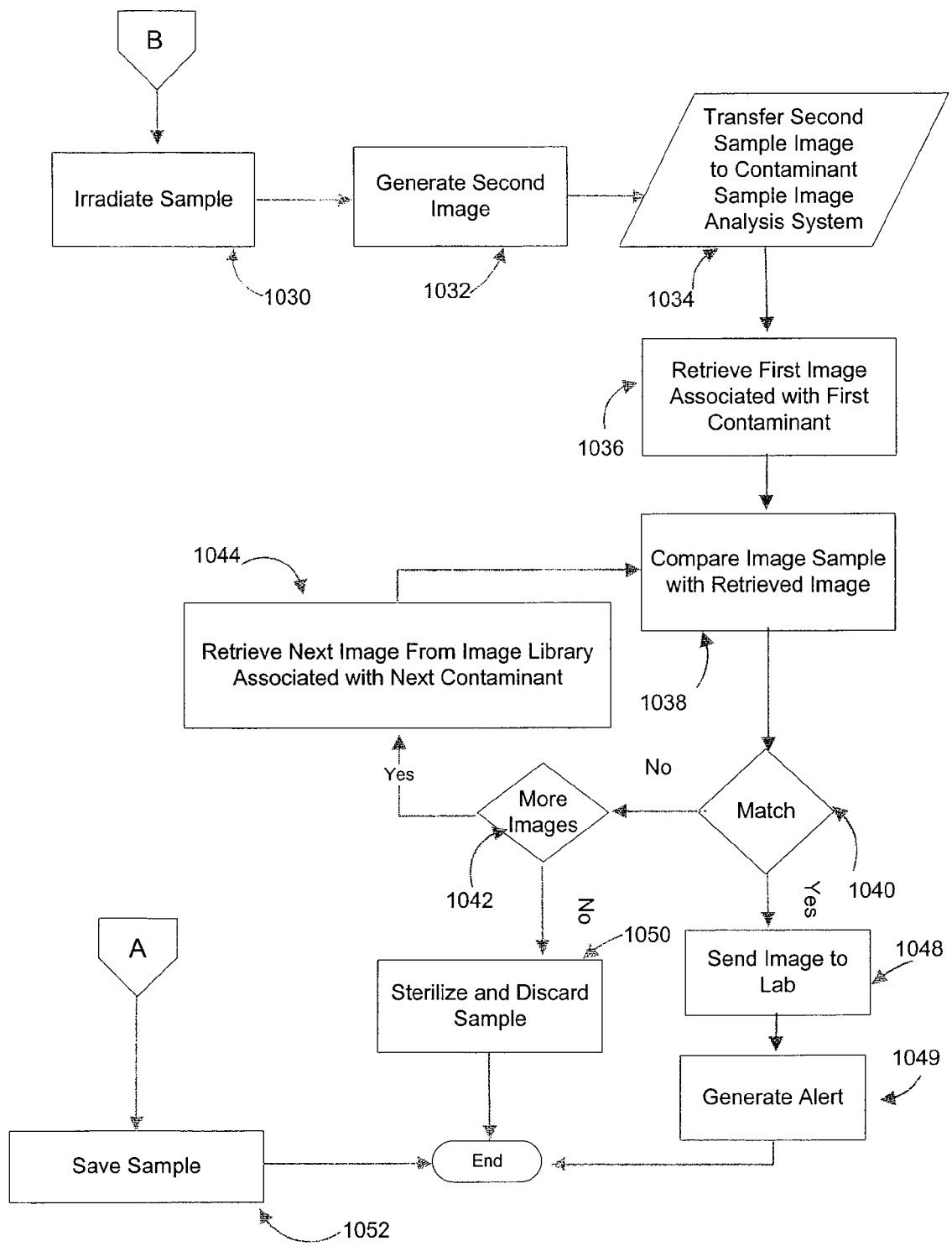

FIGS. 10a and 10b depicts a flow diagram illustrating an exemplary process 1000 performed by the airborne contaminant system 100 embodying the contaminant sample separation system 600 to capture an air sample, separate candidate contaminants or particles, and alert a remote authority in the event a contaminant is identified from among the candidate contaminants. Initially, the air capture system 102 (e.g., the centrifugal turbine or impellor 602 in the contaminant sample separation system 600) collects an air sample 116 or 604 (step 1004) and transfers the sample 116 or 604 to the indexing table 610 of the contaminant sample separation system 600 via the outlet plenum 608 and the vacuum applied to the collecting cavity 702 at the first station by the vacuum ring 606 as described above (step 1006).

After the air sample 116 or 604 is transferred to the collecting cavity 702 aligned with the first station 802, the contaminant sample separation system 600 moves the sampling cavity 702 on the indexing table 610 from the first station 802 to the second station 804 so that the an electrostatic comb 902 may be brought in frictional contact with the lower portion of the collection cavity 704 thereby imparting an electrostatic charge to a collecting surface 712 of the collecting cavity 502 (step 1008 and 1010). The electrostatic charge applied to the collecting surface 712 is effective to draw organic, chemical and other particulate matter in one plane of focus on the collecting surface 712 thereby producing a candidate sample 118.

Figure 11:
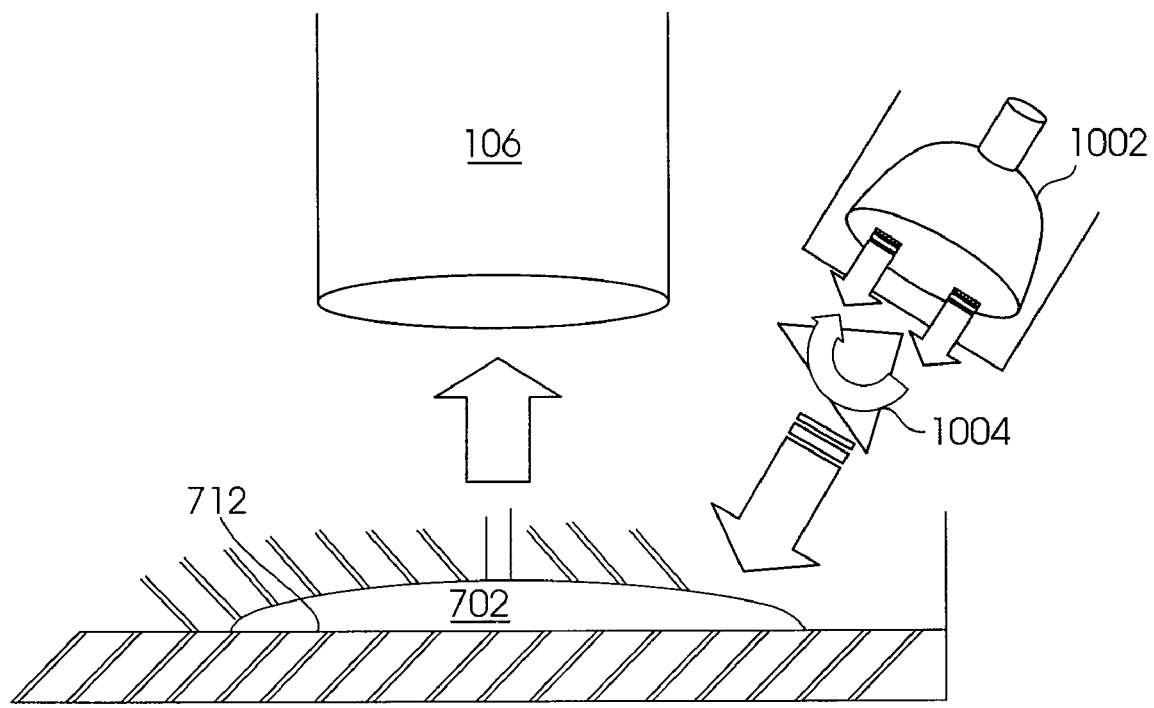
FIG. 11 is a simplified pictorial view of one embodiment of a contaminant sample imaging device of the system if FIG. 1 disposed relative to the collection cavity for generating an image of candidate particles on contaminants.

Next, the contaminant sample separation system 600 moves the collecting cavity 702 of the index table 610, containing the candidate sample 118, to the third station 806 so that the candidate sample 118 is disposed under the contaminant sample imaging device 106 in order to generate a first image 120 of the candidate sample 118 (step 1012). The generation of the candidate sample image 120 will be made with reference to FIG. 4 and FIG. 11. As previously discussed, the contaminant sample imaging device 106 may include a digital microscope 403 and a digital imager or camera 409. The digital imager 409 generates a digital image 120 of the collecting surface 704 at pre-programmed levels of magnification consistent with the lens assembly 404 of the digital imager or camera 409. The lens assembly 404 may be a micro zoom lens having variable magnification. The pre-programmed levels of magnification may be chosen as a function of the expected type of contaminant. During imaging, the collecting surface 712 of the collecting cavity 702 may also be illuminated using light generated by a full spectrum lamp source 1102 and a prismatic beam splitter or combiner 1104 disposed between the lamp source 1102 and the collecting cavity 702. The prismatic beam splitter or combiner 1104 focuses the light wavelengths of interest from the lamp source 1102 to the collecting cavity 702 that contains the candidate sample 118. The spectrum of exposure may include low-level ultraviolet frequencies. If desirable, infrared frequencies of the lamp source 1102 may be filtered by a filter (not shown). When the collecting cavity 702 containing the candidate sample 118 is aligned with the station 3 and disposed under the contaminant sample imaging device 106, the digital imager or camera 409 is prompted to generate the first image 120 of the candidate sample 118 as discussed herein.

After the first candidate sample image 120 is generated, the containment sample imaging device 106 transfers the candidate sample image 120 to the contaminant sample image analysis system 108 (step 1014). Next, the imaging comparator 416 of the contaminant sample image analysis system 108 retrieves a first reference image (e.g. 448a) associated with a first contaminant (step 1016). The image processing computer 412 than compares the first candidate sample image 120 with the retrieved image (step 1018). The image comparator 416 then determines whether the first candidate sample image 120 substantially matches the retrieved image (step 1020). If a match does not occur, the image comparator 416 determines whether there are more reference images in the image library 442 (step 1022). If there are more reference images in the image library 442, the image comparator 416 retrieves a next reference image file (e.g. 448n) from the image library 442 for comparison against the candidate sample image 120 (step 1024) before continuing processing at step 1018.

If a match occurs, the image comparator 416 generates an alert over the network 112 to a remote authorities or third party client 128 using the address 415 stored in memory, such as the local police or fire department so that the authorities or third party may evacuate the area or perform some other action to control the spread of the contaminant (step 1027). In addition, the image comparator 416 transmits the candidate sample image 120 to a contaminant testing lab 114 (step 1026) which may independently verify the candidate sample image 120 in response to the identified contaminant. Next, the image comparator 416 may rerun the steps 1018, 1020, 1022 and 1024 to verify that the candidate sample image 120 matches the retrieved image previously determined to contain a identified contaminant (step 1028). If a match is verified, the candidate sample 118 is saved along with a candidate sample image 120 before processing ends (step 1052).

If no match occurs in the first test comparison corresponding to step 1020, or no match occurs in the second test comparison corresponding to step 1028, or if no more reference images are found in the image library 422 corresponding to step 1022, the collecting cavity is rotated to the fourth station 808 where the candidate sample 118 is irradiated by ultraviolet irradiation. (step 1030). Many contaminants exhibit phosphorescence and/or fluorescence when exposed to radiation. Fluorescence and phosphorescence is generally caused by excited atoms emitting visible light when exposed to irradiation. An atom of a fluorescent material returns to its normal energy level upon removal of the irradiation, while an atom of a phosphorescent material may remain at an elevated energy level for quite some time after the removal of the irradiation. Thus, upon irradiation of the collecting surface 712, fluorescence results in the emission of visible light by contaminants in the candidate sample 118 when exposed to the irradiation. When the irradiation is removed the contaminants in the contaminant sample 118 stops emitting visible light.

The level of the irradiation in the fourth station 808 is generally set at a level and exposure time that permits excitation of the molecular structure of the contaminant while not destroying the contaminant. Both long and short wave ultraviolet irradiation may take place. Suitable irradiation sources include a tunable laser, a filtered broadband white light source or an RF energy source.

Next, the contaminant sample image device 118 moves the collection cavity 802 to the fifth station of the indexing table 810 where the contaminant sample imaging device 106 generates a image of the irradiated candidate sample 120 (step 1032). During this process, the collecting surface 712 is imaged while being irradiated to detect the presence of fluorescence. In one implementation, a third image of the collecting surface 712 my be generated following removal of the irradiation to check for the presence of phosphorescence.

After the first candidate sample image 120 is generated, the containment sample imaging device 106 transfers the candidate sample image 120 to the contaminant sample image analysis system 108 (step 1034). Next, the imaging comparator 416 of the contaminant sample image analysis system 108 retrieves a first reference image (e.g. 448a) associated with a first contaminant (step 1036). The image processing computer 412 than compares the second candidate sample image 120 with the retrieved image (step 1038). The image comparator 416 then determines whether the second candidate sample image 120 substantially matches the retrieved image (step 1040). If a match does not occur, the image comparator 416 determines whether there are more reference images in the image library 442 (step 1042). If there are more reference images in the image library 442, the image comparator 416 retrieves a next reference image file (e.g. 448n) from the image library 442 for comparison against the second candidate sample image 120 (step 1044) before continuing processing at step 1038.

If a match occurs, the image comparator 416 generates an alert over the network 112 to a remote authorities or third party client 128 using the address 415 stored in memory, such as the local police or fire department so that the authorities or third party may evacuate the area or perform some other action to control the spread of the contaminant (step 1049). In addition, if a match occurs, the image comparator 416 transmits the candidate sample image 120 to a contaminant testing lab 114 (step 1048) which may independently verify the candidate sample image 120 in response to the identified contaminant.

If no more reference images are found in the image library 422 corresponding to step 1042, the candidate sample 118 is sterilized and discarded. (step 1050).

In one implementation, upon the detection of a contaminant in the candidate image sample 120 the image comparator 416 may generate a visual alarm on display 420 and or a audible alarm via audio speaker 421 concurrently with alerting the remote authority 128 in process steps 521, 1027 and 1049. The image processing computer 412 may also be used to generate control signals (not shown in figures) to provide automatic operation of air handling equipment such as the opening or closing of dampers, the initiation of irradiation or sterilization units, and the like. In addition, the image processing computer 412 may be integrated with atmospheric weather equipment to determine the source of the contamination.

The indexing table 610 may be rotated around a common center using any conventional motor means that affords precision control. For example, the indexing table 610 may be rotated by a synchronous motor to enable stepped positioning and accuracy control.

In another embodiment of the present application, a single collecting cavity is used for all samples and the cyclic process of sampling and imaging is substantially continuous.

In order to maintain the compact size of the air borne contaminant system 100, several of the stations 802-812 may be combined. For example, the sixth 812 and first 802 stations may be combined so that the sterilization of the sample and subsequent evacuation of the collecting cavity applies a vacuum to the collecting cavity in preparation for receiving the next sample.

In one embodiment, the same irradiation source, with appropriate filters, may be used for irradiation and sterilization.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

What is claimed:

1. A method implemented using a processor and a memory, for detection of an airborne contaminant in an atmospheric environment, comprising:

capturing an air sample from the atmospheric environment;

separating candidate particles of interest from particles of non interest in the air sample by using means effective to bind particles of interest to a surface to form a candidate sample;

generating an image of the candidate sample;

identifying a contaminant from among candidate contaminants in the candidate sample using the processor by comparing the image of the candidate sample with a plurality of reference images stored in the memory; and notifying a remote third party in response to detecting the contaminant from among the candidate contaminants.

2. The method of claim 1, wherein the particles of interest are separated from particles of non interest using immunomagnetic beads effective to bind to the particles of interest, and an electromagnet is effective to hold the immunomagnetic beads and particles of interest while non-particles of interest are removed.

3. The method of claim 1, wherein the particles of interest are separated from particles of non interest using an electrostatic charge effective to bind to the particles of interest to a collection cavity.

4. A system for detection of an airborne contaminant in an atmospheric environment, comprising:

an air sample capture system configured to receive an air sample from the atmospheric environment;

a contaminant sample separation system effective to receive the air sample from the air sample capture system and to separate particles of interest from particles of non interest in the air sample by using means effective to bind particles of interest to a surface;

a contaminant sample imaging device effective to receive a particle of interest from the contaminant sample separation system and generate an image of the particle of interest to form a candidate sample image; and a contaminant sample imaging analyzing system effective to receive the candidate sample image from the contaminant sample imaging system and to detect the presence of a contaminant in the candidate sample by comparing the candidate sample image with a plurality of stored reference images.

5. The system of claim 4, further comprising a plurality of immunomagnetic beads configured to bind with the particles of interest; and an electromagnet configured to attract the immunomagnetic beads while the particles of non interest are removed.

6. The system of claim 4, further comprising a collection cavity coupled to an electrostatic generator effective to attract particles of interest to a collection cavity.

* * * * *